United States Patent [19]

Ienaga et al.

[11] Patent Number: 4,708,954
[45] Date of Patent: Nov. 24, 1987

[54] HYPOGYLCEMIC OXALURIC ACID DERIVATIVES

[75] Inventors: Kazuharu Ienaga; Ko Nakamura; Akira Ishii, all of Hyogo, Japan

[73] Assignee: Nippon Zoki Pharmaceutical Co., Ltd., Osaka, Japan

[21] Appl. No.: 826,997

[22] Filed: Feb. 7, 1986

[30] Foreign Application Priority Data

Feb. 9, 1985 [JP] Japan .................................. 60-24010

[51] Int. Cl.⁴ .................. A61K 31/535; C07D 295/20
[52] U.S. Cl. .................................... 514/183; 514/235; 514/255; 514/315; 514/423; 514/529; 514/530; 514/531; 514/551; 514/563; 544/169; 544/390; 546/245; 548/538; 548/966; 560/118; 560/121; 560/123; 560/124; 560/125; 560/169; 562/500; 562/503; 562/505; 562/506; 562/507; 562/560
[58] Field of Search ................ 546/245; 548/538, 966; 544/168, 390; 562/500, 503, 505, 506, 507, 560; 560/118, 121, 123, 124, 125, 169; 514/183, 235, 255, 315, 423, 551, 530, 531, 529, 563

[56] References Cited

PUBLICATIONS

Chemical Abstracts, 66:75960j, (1967), [S. Moshchitskii et al., 2H. Org. Khim., 2(12), 2164–7, (1966)].
Chemical Abstracts, 57:14218f, (1962), [C. Shepherd, Australian J. Biol. Sci., 15, 483, (1962)].
Chemical Abstracts, 50:3225c, (1956), [J. Andrews et al., Arch. Biochem. and Biophys. 56, 405, (1956)].
Chemical Abstracts, 57:9846c, (1962), [N. Poddubnaya et al., 2H. Oshch. Khim. 31, 3820, (1961)].
Chemical Abstracts, 25:1830, (1931), [T. Johnson et al., J. Am. Chem. Soc., 53, 1082, (1931)].
Chemical Abstracts, 19:2933, (1925), [K. Slotta, J. Prakt. Chem., 110, 264, (1925)].
Chemical Abstracts, 18:531, (1924), [M. Biltz et al., J. Prakt. Chem., 106, 108, (1923)].

Primary Examiner—Richard A. Schwartz
Attorney, Agent, or Firm—Birch, Stewart, Kolasch & Birch

[57] ABSTRACT

Pharmaceutical compositions containing an oxaluric acid derivative of the formula:

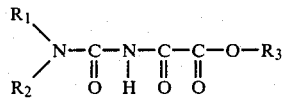

wherein each of $R_1$ and $R_2$, which may be the same or different, is hydrogen; an alkyl group or a cycloalkyl group; or $R_1$ and $R_2$ are joined to form a heterocyclic ring with the nitrogen atom to which they are both attached; and $R_3$ is hydrogen or an alkyl group. These compounds have excellent hypoglycemic effects with low toxicity and safety.

11 Claims, No Drawings

HYPOGYLCEMIC OXALURIC ACID DERIVATIVES

DETAILED DESCRIPTION OF THE INVENTION

Oral sulfonylureas and biguanides having hypoglycemic effect, have been conventionally used for the treatment of diabetes, but they tend to promote certain side effects such as excessive hypoglycemia and lactic acidosis. Insulin, a well-known antidiabetic, can only be administered intravenously due to its chemical nature, and therefore, is troublesome and inconvenient to use.

As a result of the investigations for orally administrable hypoglycemic compounds having greater safety than known compounds in order to solve the problem mentioned above, the inventors have found that oxaluric acid derivatives and pharmaceutically acceptable salts thereof have excellent hypoglycemic effect, i.e., they lower an abnormally high level of blood sugar to a normal level without excessive hypoglycemia. They have low toxicity and great safety.

An object of the present invention is to provide new, extremely safe, and orally administrable oxaluric acid derivatives and pharmaceutically acceptable salts thereof which have hypoglycemic effect, as well as low toxicity and less side effects than conventional compounds. Another object is to provide pharmaceutically compositions containing these oxaluric acid derivatives or pharmaceutically acceptable salts thereof as an active ingredient.

The novel oxaluric acid derivatives of the present invention are represented by the following formula (I):

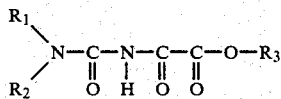

wherein each of $R_1$ and $R_2$, which may be the same or different, is hydrogen, an alkyl group, a cycloalkyl group, or $R_1$ and $R_2$ are joined to form a heterocyclic ring with the nitrogen atom from which they are both attached, and $R_3$ is hydrogen or an alkyl group.

Each of $R_1$ and $R_2$, which may be the same or different, is hydrogen, an alkyl group, preferably a straight or branched alkyl group having 1 to 20 carbon atoms, such as methyl, ethyl, propyl, iso-propyl, butyl, iso-butyl, sec-butyl, tert-butyl, pentyl, iso-pentyl, neo-pentyl, tert-pentyl, hexyl, iso-hexyl, dimethylbutyl, heptyl, octyl, nonyl, decyl or stearyl; a cycloalkyl group, preferably having 3 to 8 carbon atoms such as cyclopropyl, cyclobutyl, cyclopentyl, cyclohexyl, cycloheptyl or cyclooctyl; or $R_1$ and $R_2$ are joined to form a heterocyclic ring with the nitrogen atom they are both attached to, preferably aziridino, pyrrolidino, piperidino, piperazino or morpholino.

$R_3$ is hydrogen or an alkyl group preferably a straight or branched alkyl group having 1 to 20 carbon atoms, such as methyl, ethyl, propyl, iso-propyl, butyl, iso-butyl, sec-butyl, tert-butyl, pentyl, iso-pentyl, neo-pentyl, tert-pentyl, hexyl, iso-hexyl, dimethylbutyl, heptyl, octyl, nonyl, decyl or stearyl.

Preferred compounds of the present invention are indicated as follows:
5-methyloxaluric acid ammonium salt
5-ethyloxaluric acid ammonium salt
5-butyloxaluric acid
5-iso-butyloxaluric acid
5-tert-butyloxaluric acid
5-hexyloxaluric acid
5-(1,3-dimethyl)oxaluric acid
5-decyloxaluric acid
5-cyclopentyloxaluric acid
5-cyclohexyloxaluric acid
5-methyloxaluric acid methyl ester
5-methyloxaluric acid ethyl ester
5-butyloxaluric acid methyl ester
5-iso-butyloxaluric acid ethyl ester
5,5-dimethyloxaluric acid methyl ester
5,5-dimethyloxaluric acid ethyl ester
5-cyclohexyloxaluric acid ethyl ester
N-(1-piperidylcarbonyl)oxamic acid methyl ester
N-(1-piperidylcarbonyl)oxamic acid ethyl ester
5-methyloxaluric acid butyl ester
5-methyloxaluric acid iso-butyl ester
5-methyloxaluric acid octyl ester
5-butyloxaluric acid butyl ester
5-cyclohexyloxaluric acid iso-propyl ester
5-cyclohexyloxaluric acid butyl ester The oxaluric acid derivatives of the present invention include pharmaceutically acceptable salts of the compounds of the above-mentioned formula (I) with alkali metals such as sodium or potassium, with alkaline earth metals such as calcium and barium, with other metals such as aluminium, with ammonium, or with organic amines.

In addition, the oxaluric acid derivatives of the invention include their metal complexes, for example, complexes with zinc, iron, etc.

These salts can be prepared from free oxaluric acid derivatives or other salts of these derivatives by known methods.

When optical isomers exist in the compound of the present invention, the present invention includes any of the dl-, l - and d-isomers.

The oxaluric acid derivatives of the present invention can be prepared by art-recognized methods as indicated herein below.

(1) Oxalyl chloride and N-monoalkylurea are stirred in an appropriate solvent such as tetrahydrofuran which does not inhibit the reaction in an ice-water bath or at room temperature; or diethyl oxalate and N-monoalkylurea are stirred in an appropriate solvent which does not inhibit the reaction in the presence of an organic base such as amine or alkali metal alkoxide at room temperature, or if desired, by heating to higher temperature to give N-alkylimidazolidintrione. The resulting compound is suspended in an appropriate basic solvent such as ammonia water, and then the solution is stirred at room temperature, or if desired, by heating to higher temperature to give the desired oxaluric acid derivatives of the present invention.

The above-mentioned N-alkylimidazolidintrione can be obtained by normal N-alkylations, e.g., non-substituted imidazolidinetrione is reacted with a halogenated alkyl such as methyl iodide.

(2) N-monoalkylurea, N-monocycloalkylurea or N,N'-dialkylurea, wherein two alkyl groups are joined to form a hetero cyclic ring with the nitrogen atom to which they are both attached, and an alkyloxalyl chloride are stirred in an appropriate solvent such as tetrahydrofuran which does not inhibit the reaction in an ice-water bath or at room temperature to give the desired oxaluric acid derivatives (3) Water or alcohol is reacted with oxalyl chloride with stirring, in an appropriate solvent such as tetrahydrofuran which does not inhibit the reaction, in an ice-water bath or at room temperature. N-monoalkylurea, N-monocycloalkylurea or N,N'-dialkylurea, wherein two alkyl group are joined to form a hetero cyclic ring with the nitrogen atom to which they are both attached, is added to the solution, and the reaction mixture is further stirred in an ice-water bath or at room temperature to give the desired compounds of the present invention.

The resulting compounds of the present invention are purified by usual methods such as distillation, chromatography and recrystallization. They are identified by elemental analysis, melting point, IR, NMR, UV and mass spectra.

The following examples, which are illustrative and not intended to limit the scope of the invention, describe the preparation of the compounds of the present invention.

EXAMPLE

Example 1

6.6 g of methylurea was added to 200 ml of anhydrous tetrahydrofuran and the suspension was stirred in an ice-water bath. 12.5 g of oxalyl chloride was added dropwise to the suspension, and the stirring was continued for 30 minutes in an ice-water bath. 200 ml of ethyl acetate and 70 ml of water were added to the reaction mixture and the organic layer was obtained by extraction. The water layer was further extracted with 130 ml of ethyl acetate. The resulting organic layer was dried over anhydrous sodium sulfate and evaporated to dryness, and the crude residue was recrystallized from ethyl acetate-hexane to give 10.0 g of 1-methylimidazolidinetrione in the form of colorless needle crystals. The resulting compound was stirred in 1N ammonia water for a hour at room temperature. The solution was evaporated to dryness and the residue was recrystallized from water-ethanol to give 7.7 g of 5-methyloxaluric acid ammonium salt (compound 1) in the form of colorless prism crystals.

m.p.: 197°–201° C.
IR(KBr): 3240, 1698, 1626, 1428, 785 cm$^{-1}$
NMR(DMSO-d$_6$):$\delta$=2.70(d,3H,J=5.4 Hz), 7.23(brs,4H), 8.04(brs,1H), 9.50(brs,1 H)
MS (m/z) (SIMS): 147 (M$^+$+1) (free form)

In the same way, the following compound was obtained.
5-ethyloxaluric acid ammonium salt (compound 2)
m.p.: 158°–160° C.
IR(KBr): 3320, 3230, 1700, 1680, 1635, 788 cm$^{-1}$
NMR(DMSO-d$_6$):$\delta$=1.05(t,3H,J=7.3 Hz), 3.16(dq,2H,J=7.3 Hz), 7.26(brs,4H), 8.13(brt,1H,J=7.3 Hz), 9.43(brs,1H)
MS (m/z): 160 (M$^+$), 145, 115, 90, 72, 44, 30 (free form)

Example 2

3.6 g of butylurea was added to 100 ml of anhydrous tetrahydrofuran and the suspension was stirred in an ice-water bath. 4.3 g of oxalyl chloride was added dropwise to the suspension, and the stirring was continued for 30 minutes in an ice-water bath. 100 ml of ethyl acetate and 30 ml of water were added to the reaction mixture and the organic layer was obtained by extraction, The water layer was further extracted with 60 ml of ethyl acetate. The resulting organic layer was dried over anhydrous sodium sulfate and evaporated to dryness, the crude residue was recrystallized from ethyl acetate-hexane to give 5.1 g of 1-butylimidazolidinetrione in the form of colorless needle crystals. The resulting compound was suspended to 400 ml of 0.1N ammonium aqueous solution and stirred for 8 hours at room temperature. Further, 5 ml of 28% ammonium aqueous solution was added to the solution and stirred for 14 hours. The solvent was distilled off under reduced pressure and the residue was dissolved in methanol. 3 ml of conc. hydrochloric acid was added thereto. The solution was concentrated under reduced pressure, and the solid precipitate was filtered off, washed with water sufficiently, and recrystallized from water-methanol to give 1.8 g of 5-butyloxaluric acid (compound 3) in the form of colorless needle crystals.

m.p.: 166° C. (decomposition)
IR(KBr): 3340, 3220, 2950, 2850, 2800–2100, 1710, 1650, 1540 cm$^{-1}$
NMR(DMSO-d$_6$): $\delta$=0.87(t,3H,J=7.2 Hz), 1.27(tq,2H,J$_1$=7.2 Hz,J$_2$=7.2 Hz), 1.42(tt,2H,J$_1$=7.2 Hz,J$_2$=7.2 Hz), 3.12(dt,2H,J=7.2 Hz), 7.83(brs,1H), 10.36(s,1H)
MS (m/z): 188 (M$^+$), 159, 145, 90, 72, 57, 44, 30

In the same way, the following compounds were obtained.
5-iso-butyloxaluric acid (compound 4)
m.p.: 171.5 ° C. (decomposition)
IR(KBr): 3360, 3280, 2950, 2860, 2800–2200, 1760, 1680, 1555 cm$^{-1}$
NMR(DMSO-d$_6$):$\delta$=0.84(d,6H,J=6.8 Hz), 1.72(m,1H), 2.97(dd,2H,J=6.8 Hz), 7.89(brs,1H), 10.38(s,1H)
MS (m/z): 188 (M$^+$), 145, 133, 90, 72, 57, 44, 30
5-tert-butyloxaluric acid (compound 5)
m.p.: 159°–162° C.
IR(KBr): 3200, 2950, 1702, 1660, 1545, 1175 cm$^{-1}$
NMR(DMSO-d$_6$):$\delta$=1.28(s,9H), 7.80(brs,1H), 10.25(brs,1H)
MS (m/z): 188 (M$^+$), 173, 130, 90, 84, 58
5-hexyloxaluric acid (compound 6)
m.p.: 167° C. (decomposition)
IR(KBr): 3360, 3280, 2950, 2920, 2850, 2800–2300, 1760, 1670, 1545 cm$^{-1}$
NMR(DMSO-d$_6$):$\delta$=0.85(t,3H,J=6.8 Hz), 1.24(s,6H), 1.43(m,2H), 3.12(dt,2H), 7.86(brs,1H), 10.36(s,1H)
MS (m/z): 216 (M$^+$), 170, 145, 133, 100, 90, 44, 30
5-(1,3-dimethylbutyl)oxaluric acid (compound 7)
m.p.: 156° C. (decomposition)
IR(KBr): 3360, 3300, 2950, 2800–2200, 1770, 1690, 1550 cm$^{-1}$
NMR(DMSO-d$_6$):$\delta$=0.84(d,3H,J=6.8 Hz), 0.85(d,3H,J=6.8 Hz), 1.07(d,3H,J=6.4 Hz), 1.21(m,1H), 1.37(m,1H), 1.57(m,1H), 1.57(m,1H), 3.77(brs,1H), 7.64(brs,1H), 10.33(s,1H)
MS (m/z): 216 (M$^+$), 170, 145, 133, 100, 90, 44, 30
5-decyloxaluric acid (compound 8)
m.p.: 160°–161° C.
IR(KBr): 3375, 3280, 2910, 2850, 2800–2200, 1760, 1675, 1540 cm$^{-1}$
NMR(DMSO-d$_6$):$\delta$=0.84(t,3H,J=6.8 Hz), 1.23(s,14 Hz), 1.42(m,2H), 3.11(dt,2H), 7.86(brs,1H), 10.35(s,1H)
MS (m/z): 272 (M$^+$), 171, 156, 145, 133, 113, 99, 90, 84, 56, 44, 30
5-cyclopentyloxaluric acid (compound 9)
m.p.: 172.5° C. (decomposition)

IR(KBr): 3375, 3280, 2950, 2860, 2800–2300, 1765, 1680, 1545 cm$^{-1}$

NMR(DMSO-d$_6$):δ=1.40(m,2H), 1.50–1.64(m,4H), 2.49(m,2H), 3.95(m,1H), 7.78(brs,1H), 10.3(s,1H)

MS (m/z): 200 (M+), 171, 154, 133, 128, 90, 84, 69, 59, 44, 41

5-cyclohexyloxaluric acid (compound 10)

m.p.: 173° C. (decomposition)

IR(KBr): 3355, 3290, 2920, 2850, 2800–2300, 1765, 1675, 1540 cm$^{-1}$

NMR(DMSO-d$_6$):δ=1.13–1.34(m,5H), 1.5 (m,1H), 1.61(m,2H), 1.77(m,2H), 3.51(brs,1H), 7.77(brs,1H), 10.36(s,1H)

MS (m/z): 214 (M+), 171, 133, 128, 98, 90, 82, 67, 56, 44, 41

Example 3

After 7.4 g of methylurea was suspended in 200 ml of tetrahydrofuran, 11 ml of methyloxalyl chloride was added dropwise for 30 minutes to the suspension with stirring in an ice-water bath, and the solution was stirred for 30 minutes in an ice-water bath and then for 7 hours at room temperature. The precipitate was filtered off, washed with water, dried, and recrystallized from ethyl acetate to give 10.2 g of 5-methyloxaluric acid methyl ester (compound 11).

m.p.: 146.5° C. (decomposition)

IR(KBr): 3360, 3300, 2950, 1710, 1695, 1520 cm$^{-1}$

NMR(DMSO-d$_6$):δ=2.67(d,3H,J=4.4 Hz), 3.77(s,3H), 7.78(brs,1H), 10.62(s,1H)

MS (m/z): 160 (M+), 101, 89, 70, 58, 44, 30, 15

In the same way, the following compounds were obtained.

5-methyloxaluric acid ethyl ester (compound 12)

m.p.: 149°–150° C.

IR(KBr): 3335, 3210, 3150, 2980, 2940, 1747, 1700, 1680, 1482, 680 cm$^{-1}$

NMR(DMSO-d$_6$):δ=1.25(t,3H,J=7.2 Hz), 2.68(d,3H,J=3.5 Hz), 4.22(q,2H,J=7.2 Hz), 7.8(brs,1H), 10.6(brs,1H)

MS (m/z): 174 (M+), 145, 128, 101, 58, 44, 29

5-butyloxaluric acid methyl ester (compound 13)

m.p.: 83°–85° C.

IR(KBr): 3350, 3220, 3150, 2950, 2860, 1765, 1720, 1680, 1540 cm$^{-1}$

NMR(DMSO-d$_6$):δ=0.86(t,3H,J=7.2 Hz), 1.26(tq,2H,J=7.2 Hz), 1.4l(tt,2H), 3.11(dt,2H), 3.76(s,3H), 7.77(brs,1H), 10.53(s,1H)

MS (m/z): 202 (M+), 159, 104, 72, 57, 41, 30, 15

5-iso-butyloxaluric acid ethyl ester (compound 14)

m.p.: 82°–83° C.

IR(KBr): 3270, 2940, 1700, 1675, 1522, 1224, 690 cm$^{-1}$

NMR(DMSO-d$_6$):δ=0.84(d,6H,J=6.0 Hz), 1.25(t,3H,J=7.0 Hz), 1.72(tq,1H,J=6.0 Hz), 2.96(brt,2H,J=6.0 Hz), 4.22(q,2H,J=7.0 Hz), 7.8(brs,1H), 10.55(brs,1H)

MS (m/z): 216 (M+), 187, 173, 161, 118, 72, 57, 41

5,5-dimethyloxaluric acid methyl ester (compound 15)

m.p.: 87°–88° C.

IR(KBr): 3240, 2950, 1740, 1708, 1682, 1214 cm$^{-1}$

NMR(DMSO-d$_6$):δ=3.03(s,6H), 3.93(s,3H), 9.03(brs,1H)

MS (m/z): 174 (M+), 156, 115, 72, 59, 44

5,5-dimethyloxaluric acid ethyl ester (compound 16)

m.p.: oily substance

IR(CHCl$_3$):3360, 3000, 1760, 1722, 1684, 1180, 704 cm$^{-1}$

NMR(DMSO-d$_6$):δ=1.23(t,3H,J=7.2 Hz), 2.88(brs,6H), 4.19(q,2H,J=7.2 Hz), 10.80(brs,1H)

MS (m/z): 188 (M+), 170, 115, 88, 72, 56, 44, 29, 15

5-cyclohexyloxaluric acid ethyl ester (compound 17)

m.p.: 74.5°–75.5° C.

IR(KBr): 3300, 2930, 2850, 1720, 1685 cm$^{-1}$

NMR(CDCl$_3$):δ=1.17°–1.96(m,10H), 1.41(t,3H,J=7.5 Hz), 3.75(m,1H), 4.40(q,2H,J=7.5 Hz), 7.9(d,1H,J=5.5 Hz), 8.76(s,1H)

MS (m/z): 242 (M+), 213, 199, 161, 118, 98, 90, 83, 82, 67, 56, 41, 29

Example 4

After 12.8 g of N-carbamoylpiperidine was dissolved in 200 ml of tetrahydrofuran, 11 ml of methyloxalyl chloride was added dropwise for 30 minutes thereto with stirring in an ice-water bath, and the solution was stirred for 30 minutes in an ice-water bath and then for 7 hours at room temperature. The solution was allowed to stand overnight at room temperature. After tetrahydrofuran was distilled off under the reduced pressure, water was added to the residue and extracted with ethyl acetate. The ethyl acetate layer was washed three times with saturated aqueous solution of sodium chloride, and dried over anhydrous sodium sulfate. Ethyl acetate was distilled off and ether was added to the residue to be crystallized. The crude product was filtered off and recrystallized from ethyl acetate-hexane to give 12.9 g of N-(1-piperidylcarbonyl) oxamic acid methyl ester (compound 18).

m.p.: 92°–93° C.

IR(KBr): 3210, 2940, 2860, 1730, 1700, 1670 cm$^{-1}$

NMR(DMSO-d$_6$):δ=1.42–1.55(m,6H), 3.36(tt,4H), 3.72(s,3H), 10.92(s,1H)

MS (m/z): 214 (M+), 155, 112, 84, 70, 59, 42, 29, 15

In the same way, the following compound was obtained.

N-(1-piperidylcarbonyl)oxamic acid ethyl ester (compound 19)

m.p.: oily substance

IR(Neat): 3250, 2940, 2860, 1730, 1700, 1675 cm$^{-1}$

NMR(DMSO-d$_6$):δ=1.22(t,3H,J=7.2 Hz), 1.42–1.56(m,6H), 3.36(tt,4H), 4.1.8(q,2H,J=7.2 Hz), 10.88(s,1H)

MS (m/z): 228 (M+), 155, 112, 84, 70, 56, 41, 29

Example 5

8.5 ml of oxalyl chloride was added to 200 ml of tetrahydrofuran, 9.2 ml of butylalcohol was added dropwise for 30 minutes with stirring in an ice-water bath, and the solution was stirred for a hour in an ice-water bath. 7.4 g of methylurea was slowly added thereto and the solution was stirred for 15 hours at room temperature. After tetrahydrofuran was distilled off under the reduced pressure, water was added to the residue and extracted with ethyl acetate. The ethyl acetate layer was washed three times with saturated aqueous solution of sodium chloride, and dried over anhydrous sodium sulfate. The crude product was passed through a column of silica gel. Ethyl acetate was distilled off, and ether was added thereto. The precipitate was filtered off and recrystallized from ethyl acetate-hexane to give 11.2 g of 5-methyloxaluric acid butyl ester (compound 20).

m.p.: 105°–106° C.

IR(KBr): 3200, 2950, 2860, 1760, 1710, 1685, 1540 cm$^{-1}$

NMR(DMSO-d$_6$):δ=0.89(t,3H,J=7.6 Hz), 1.34(tq,2H,J$_1$=6.8 Hz,J$_2$=7.6 Hz), 1.62(tt,2H,J$_1$=6.8 Hz,J$_2$=7.6 Hz), 2.67(d,3H,J=4.4 Hz), 4.18(t,2H,J=6.8 Hz), 7.80(brs,1H), 10.63(s,1H)

MS (m/z): 202 (M+), 173, 128, 101, 74, 58, 41, 29

In the same way, the following compounds were obtained.

b 5-methyloxaluric acid iso-butyl ester (compound 21)

m.p.: 107°-109° C.

IR(KBr): 3350, 3220, 3140, 2950, 1750, 1730, 1690, 1555 cm$^{-1}$

NMR(DMSO-d$_6$):δ=0.90(d,6H,J=6.8 Hz), 1.95(m,1H), 2.67(d,3H,J=4.4 Hz), 3.97(d,2H,J=6.8 Hz), 7.74(brs,1H), 10.63(s,1H)

MS (m/z): 202 (M+), 128, 101, 74, 58, 57, 41, 29

5-methyloxaluric acid octyl ester (compound 22)

m.p.: 102°-103° C.

IR(KBr): 3290, 2940, 2900, 1684, 1234 cm$^{-1}$

NMR(DMSO-d$_6$):δ=0.85(t,3H,J=6.4 Hz), 1.24(brs,10H), 2.5-2.7(m,2H), 2.67(d, 3 H,J=4.5 Hz), 4.16(t,2H,J=6.4 Hz), 6.7(brs,1H), 10.62(brs,1H)

MS (m/z): 258 (M+), 157, 128, 100, 84, 71, 57, 41

5-butyloxaluric acid butyl ester (compound 23)

m.p.: 68°-69° C.

IR(KBr): 3352, 3130, 2950, 1746, 1706, 1675, 1245, 670 cm$^{-1}$

NMR(DMSO-d$_6$):δ=0.87(t,3H,J=7.0 Hz), 0.89(t,3H,J=7.0 Hz), 1.2-1.5(m,6H), 1.62(tt,2H,J$_1$=7.0 Hz,J$_2$=7.0 Hz), 3.11(m,2H), 4.18(t,2H,J=7.0 Hz), 7.7(brs,1H), 10.53(brs,1H)

MS (m/z): 244 (M+), 201, 159, 90, 72, 57, 41

5,5-cyclohexyloxaluric acid iso-propyl ester (compound 24)

m.p.: 57°-58.5° C.

IR(KBr): 3300, 3250, 3150, 2930, 2850, 1755, 1710 cm$^{-1}$

NMR(CDCl$_3$):δ=1.20-1.95(m,10H), 1.38(d,6H,J=6.5 Hz), 3.77(m,1H), 5.19(m,1H), 7.96(d,1H,J=6.7 Hz), 8.82(s,1H)

MS (m/z): 256 (M+), 213, 175, 133, 98, 90, 83, 67, 56, 43, 41

5,5-cyclohexyloxaluric acid butyl ester (compound 25)

m.p.: 68°-70° C.

IR(KBr): 3300, 2925, 2850, 1710, 1685 cm$^{-1}$

NMR(CDCl$_3$):δ=0.96(t,3H,J=7.4 Hz), 1.19-1.96(m,14H), 3.75(m,1H), 4.43(t,2H,J=6.6 Hz), 7.93(d,1H,J=7.0 Hz), 8.80(s,1H)

MS (m/z): 270 (M+), 227, 213, 189, 146, 98, 90, 83, 67, 56, 41

The following description serves to illustrate the pharmaceutical studies of the compounds of the present invention.

(1) Acute toxicity test

The test compounds of the present invention suspended in 0.5% aqueous solution of carboxymethylcellulose (C.M.C.) were orally administered to groups of 4 to 6 ddY-strain male mice (weighing about 19 g) which had fasten for 20 hours. The lethal dose was determined by the number of deaths for 7 days thereafter.

An example of the results is shown in Table 1.

TABLE 1

| Test Compound | LD$_{50}$ (mg/kg) |
| --- | --- |
| compound 2 | 3,000 to 4,000 |
| compound 13 | 1,000 to 2,000 |

TABLE 1-continued

| Test Compound | LD$_{50}$ (mg/kg) |
| --- | --- |
| compound 20 | >4,000 |

(2) Hypoglycemic effect

Groups of 7 Wistar-strain male rats (weighing about 200 g) which were fasted for 20 hours were used for measurement of the hypoglycemic effect according to the modified method by Dulin et al. [Dulin, W. L. et al., Proc. Soc. Expl. Med., 107, 245 (1961)]. That is, 0.5 ml/100 g of 20% aqueous solution of glucose was subcutaneously administered to the backs of rats to prevent a decrease in blood glucose level because of the fasting. Immediately thereafter the test drug suspended in 0.5% aqueous C.M.C. solution was orally given, and 2 hours later, the animals underwent laparotomy under pentobarbital anesthesia, then blood was drawn from the inferior vena cava. The obtained blood sample was allowed to stand for 30 minutes to complete the coagulation and was centrifuged to obtain the serum. Blood sugar level was measured according to the mutalotase GOD method [Trinder, Ann. Clin. Biochem., 6, 24 (1979)].

The results is shown in Table 2.

TABLE 2

| Test Compound | Dosage (mg/kg) | Blood Glucose Level (mg/dl) | Decrease (%) |
| --- | --- | --- | --- |
| control | — | 139 ± 3 | — |
| compound 1 | 100 | 104 ± 7 | 25.2 |
| compound 2 | 100 | 102 ± 4 | 26.6 |
| compound 3 | 100 | 103 ± 5 | 26.0 |
| compound 12 | 100 | 81 ± 5 | 41.7 |
| compound 13 | 100 | 88 ± 3 | 36.7 |
| compound 14 | 100 | 93 ± 2 | 33.1 |
| compound 20 | 100 | 101 ± 6 | 27.3 |
| compound 21 | 100 | 115 ± 4 | 17.3 |
| compound 22 | 100 | 122 ± 2 | 12.2 |
| Tolubutamide | 100 | 50 ± 1 | 64.0 |

As shown by the above-mentioned results, the compounds of the present invention have an excellent hypoglycemic effect. The compounds of the invention are extremely useful as drugs to improve severe hyperglycemia since, even at high doses, they maintain the blood sugar at steady levels. Moreover, the novel compounds have low toxicity and great safety, so that its long-term continuous administration and oral use are possible. Therefore, the compounds are not only useful as antidiabetics, but also as drugs for various diseases caused by diabetes, e.g., diabetic angiopathy, such as diabetic arteriosclerosis, diabetic retinitis, diabetic nephropathy, diabetic neurosis and diabetic microangiopathy.

The compounds of the present invention may be made into pharmaceutical compositions by combination with appropriate medicial carriers or diluents, and may be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention may be used in the form of their pharmaceutically acceptable salts, and also may be used alone or in appropriate association, as well as in combination with other pharmaceutically active components.

In case of oral preparations, the compounds may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, they may be made into suppositories by mixing with a variety of bases such as emulsifying bases or water-soluble bases.

The compounds of the present invention may be formulated into preparations for injections by dissolving, suspending or emulsifying them in aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In case of inhalations or aerosol preparations, the compounds of the invention in the form of a liquid or minute powder may be filled up in an aerosol container with gas or liquid spraying agents, and if desired, with conventional adjuvants such as humidifying agents added. They may also be applied as pharmaceuticals for non-pressurized preparation such as in a nebulizer or an atomizer.

Cataplasms may be prepared by mixing the compounds with mentha oil, concentrated glycerin, kaolin or other suitable additives.

The desirable dose of the oxaluric acid derivatives of the present invention varies with the subject, drug form, method and period of administration. However, in order to obtain desirable effects, generally it is recommended to administer orally 1 to 1000 mg, preferably 5 to 600 mg daily. Unit preparations containing appropriate amounts of the compounds of the present invention are also recommended to administer by 1 to several units daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

| Prescription example 1 (tablet) | |
|---|---|
| Component | Content in a tablet (mg) |
| an invented compound | 100 |
| lactose | 130 |
| corn starch | 40 |
| magnesium stearate | 10 |
| Total | 280 mg |

| Prescription example 2 (capsule) | |
|---|---|
| Component | Content in a capsule (mg) |
| an invented compound | 50 |
| lactose | 250 |
| Total | 300 mg |

| Prescription example 3 (injection) | |
|---|---|
| Component | Content in an ampule (mg) |
| an invented compound | 10 |
| sodium chloride | proper amount |
| distilled water for injection | proper amount |
| Total | 1 ml |

| Prescription example 4 (ointment) | |
|---|---|
| Component | Weight (g) |
| an invented compound | 1 |
| emulsified wax | 30 |
| white petrolatum | 50 |
| liquid paraffin | 20 |
| Total | 101 g |

| Prescription example 5 (suppository) | |
|---|---|
| Component | Content in a suppository (mg) |
| an invented compound | 20 |
| cacao butter | 1980 |
| Total | 2000 mg |

What is claimed is:

1. An oxaluric acid derivative of the formula (I):

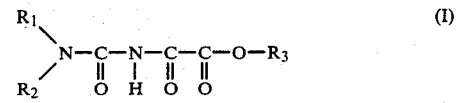

wherein $R_1$ is an alkyl group having 1 to 20 carbon atoms or a cycloalkyl group having 3 to 8 carbon atoms; $R_2$ is hydrogen, an alkyl group having 1 to 20 carbon atoms or a cycloalkyl group having 3 to 8 carbon atoms; or $R_1$ and $R_2$ join to form an aziridino, pyrrolidino, piperazino, morpholins or piperidino group; and $R_3$ is an alkyl group having 1 to 20 carbon atoms; or a pharmaceutically acceptable salt thereof.

2. An oxaluric acid derivative according to claim 1, wherein $R_2$ is hydrogen or a pharmaceutically acceptable salt thereof.

3. An oxaluric acid derivative according to claim 2, wherein $R_1$ is an alkyl group having 1 to 20 carbon atoms or a pharmaceutically acceptable salt thereof.

4. An oxaluric acid derivative according to claim 2, wherein $R_1$ is a cycloalkyl group having 3 to 8 carbon atoms or a pharmaceutically acceptable salt thereof.

5. An oxaluric acid derivative according to claim 2, wherein $R_1$ and $R_2$ are joined to form piperidino group or a pharmaceutically acceptable salt thereof.

6. A pharmaceutical composition for treating diabetes and diseases caused by diabetes which comprises as an active ingredient an effective hypoglycemic amount of at least one oxaluric acid derivative of the formula (I):

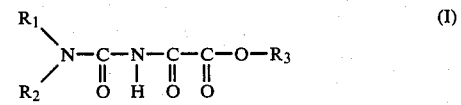

wherein $R_1$ is an alkyl group having 1 to 20 carbon atoms or a cycloalkyl group having 3 to 8 carbon atoms; $R_2$ is hydrogen, an alkyl group having 1 to 20 carbon atoms or a cycloalkyl group having 3 to 8 carbon atoms; or $R_1$ and $R_2$ are joined to form an aziridino, pyrrolidino, piperazino, morpholino or piperidino group; and $R_3$ is an alkyl group having 1 to 20 carbon atoms; or a pharmaceutically acceptable salt thereof, and an inert carrier or diluent.

7. A pharmaceutical composition according to claim 6, which is formulated for oral administration.

8. A pharmaceutical composition according to claim 6, which is formulated for parenteral administration.

9. A method for treating diabetes and diseases caused by diabetes which comprises administering to a subject an effective hypoglycemic amount of an oxaluric acid derivative of the formula (I):

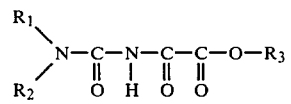

wherein each of $R_1$ and $R_2$, which may be the same or different, is hydrogen, an alkyl group having 1 to 20 carbon atoms or a cycloalkyl group having 3 to 8 carbon atoms; or $R_1$ and $R_2$ are joined to form an aziridino, pyrrolidino, piperidino, piperazino or morpholino group with the nitrogen to which they are both attached; and $R_3$ is hydrogen or an alkyl group having 1 to 20 carbon atoms; or a pharmaceutically acceptable salt thereof.

10. A method according to claim 9, wherein said oxaluric acid derivative is administered orally in a dosage of 1 to 1000 mg daily.

11. A method according to claim 9, wherein said oxaluric acid derivative is administered parenterally in a dosage of 0.1 to 333 mg daily.

* * * * *

UNITED STATES PATENT AND TRADEMARK OFFICE
CERTIFICATE OF CORRECTION

PATENT NO. : 4,708,954
DATED : November 24, 1987
INVENTOR(S) : Kazuharu IENAGA et al It is certified that error appears in the above-identified patent and that said Letters Patent is hereby corrected as shown below:

IN THE TITLE:

change "HYPOGYLCEMIC" to --HYPOGLYCEMIC--.

Signed and Sealed this

Twenty-fourth Day of May, 1988

Attest:

DONALD J. QUIGG

*Attesting Officer*  Commissioner of Patents and Trademarks